US00PP11130P

United States Patent [19]

Yomo et al.

[11] Patent Number: Plant 11,130

[45] Date of Patent: Nov. 23, 1999

[54] VERBENA PLANT NAMED 'SUNMARISA'

[75] Inventors: Yasunori Yomo, Kitakoma-gun; Yasuyuki Murakami, Gamou-gun, both of Japan

[73] Assignee: Suntory Limited, Osaka, Japan

[21] Appl. No.: 08/923,819

[22] Filed: Sep. 4, 1997

[30] Foreign Application Priority Data

Sep. 4, 1996 [JP] Japan ..... 9057

[51] Int. Cl.[6] ..... A01H 5/00

[52] U.S. Cl. ..... Plt./308

[58] Field of Search ..... Plt./87, 308

[56] References Cited

U.S. PATENT DOCUMENTS

P.P. 8,995 11/1994 Tachibana et al. ..... Plt./87
P.P. 9,014 12/1994 Tachibana et al. ..... Plt./87
P.P. 9,059 2/1995 Tachibana et al. ..... Plt./87
P.P. 9,085 3/1995 Tachibana et al. ..... Plt./87
P.P. 9,121 4/1995 Tachibana et al. ..... Plt./87
P.P. 9,411 12/1995 Tachibana et al. ..... Plt./87

OTHER PUBLICATIONS

GTITM UPOVROM Citation for 'Sanmarisa' as per JP PBR 9057, Sep. 4, 1996.

*Primary Examiner*—Howard J. Locker
*Assistant Examiner*—Kent L. Bell
*Attorney, Agent, or Firm*—Burns, Doane, Swecker & Mathis, L.L.P.

[57] ABSTRACT

Disclosed herein is a verbena plant which has a broad spreading growth habit and long stems. The plant forms flowers in clusters with a great profusion of blooms. The blooming period is late April to November and flowering duration is long. The entire plant remains in bloom for an extended period of time. The flower size is large and the petal color of the flowers is light purplish pink. The plant is highly tolerant to heat, and exhibits a high resistance to pests and diseases, particularly powdery mildew, and a high resistance to rain.

2 Drawing Sheets

BACKGROUND OF THE VARIETY

The present invention provides a new and distinct variety of *Verbena hybrida* plant obtained from crossing a *Verbena hybrida* named 'Amour White' (non-patented in the United States) (♀) and a wild type of verbena plant *Verbena peruviana* (♂) native to Brazil.

The verbena is a very popular plant and is used for flower bedding and potting in the summer season. There are only a few varieties of Verbena plants which have a spreading growth habit, much branching, a large number of flowers in a cluster and which have a high resistance to rain, heat, cold and diseases. Accordingly, this invention was aimed at obtaining a new variety having a spreading growth habit, strong branching, a large number of flowers in a cluster, a flower of large diameter, a high tolerance to heat and cold, and resistance to diseases and pests, and also having petals that are light purplish pink.

The new variety of verbena plant according to this invention originated from crossing a Verbena hybrida plant named 'Amour White' (♀) and a wild type of verbena plant Verbena peruviana (♂) that is native to Brazil.

Initially, 38 seedlings were obtained in the autumn of 1994, following the crossing of 'Amour White' as the female parent and a wild type of verbena plant (*Verbena peruviana f. rosea*) as the pollen parent in the May of 1994. From this crossing, 3 seedlings were selected in view of their spreading growth habit and were propagatged by cuttings, and then grown as a trial in flower beds and planters beginning in the spring of 1995. Finally one seedling was selected in the autumn of 1995 and the botanical characteristics were examined, using the varieties 'Sumaripi' (non-patented in the United States) and 'Derby Salmon Rose' (non-patented in the United States) for comparison. As a result, it was concluded that this Verbena is distinguishable from any other variety, whose existence is known to us, and is uniform and stable in its characteristics. The new variety of verbena plant of the present invention was named 'Sunmarisa'.

In the following description, the color-coding is in accordance with the Horticultural Colour Chart of The Royal Horticultural Society, London, England (R.H.S. Colour Chart), and the Inter-Society color Council-Nation Bureau of Standard Color Name (I.S.C.C.-N.B.S. Color Name). A color chart based on The Japan Color Standard for Horticultural Plant (J.H.S. Color Chart) is also added for reference.

'Armour White' was used as the female parent when obtaining this new variety 'Sunmarisa'. 'Armour White' has an erect growth habit and is publicly available.

The pollen parent used in obtaining this new variety 'Sunmarisa' was a wild type of *Verbena peruviana* native to South Brazil. This wild type of verbena plant is presently maintained at the Hakushu Nursery Center of SUNTORY Ltd., 2913-1 Torihara, Hakushu-cho, Kitakoma-gun, Yamanashi-ken, Japan. The main botanical characteristics of this pollen parent are as follows when grown at the Hakushu Nursery Center of SUNTORY ltd., 2913-1 Torihara, Hakushu-cho, Kitakoma-gun, Yamanashi-ken, Japan.

Plant:
- *Growth habit.*—Spreading.
- *Plant height.*—10–20 cm.
- *Plant extension.*—100–150 cm.

Stem:
- *Diameter.*—1.0–2.0 mm.
- *Anthocyanin pigmentation.*—Present.
- *Branching.*—Medium.
- *Pubescence.*—Medium.
- *Length of internode.*—3.0–4.0 cm.

Leaf:
- *Phyllotaxis.*—Opposite.
- *Shape of blade.*—Hastate.
- *Length.*—3.0–4.0 cm.

*Width.*—1.5–2.0 cm.
*Depth of incision.*—Shallow.
*Color.*—Moderate olive green (R.H.S. 146A, J.H.S. 3509).
*Pubescence.*—Slight.

Flower:
*Facing direction.*—Upward.
*Outward curvature of petal.*—Slightly curved.
*Diameter.*—2.0–3.0 cm.
*Height.*—20–30 mm.
*Color.*—Strong reddish purple (R.H.S. 77B, J.H.S. 8911).
*Color presentation.*—Substantially even.
*Overlapping of petals.*—Opened.
*Flower cluster.*—30–40 mm in length; and 50–60 mm in diameter.
*Calyx.*—1.5–2.0 cm in length.
*Anthocyanin pigmentation of calyx limb.*—Absent.
*Peduncle.*—1–2 mm in thickness; and 3.0–5.0 cm in length.
*Number of flowers.*—Plentiful (approximately 10–14)
*Reproductive organs.*—1 pistil and 4 stamens.
*Flower fragrance.*—Absent.
*Flowering duration.*—Short.

Physiological and ecological characteristics: High resistance to diseases and pests and high tolerance to heat and cold.

The 'Sunmaripi' variety was used as a comparison for this new 'Sunmarisa' variety. The main botanical characteristics of the 'Sunmaripi' variety are as follows when grown at Hakushu Nursery Center of SUNTORY Ltd. at 2913-1, Torihara, Hakushu-cho, Kitakomo-gun, Yamanishi-ken, Japan.

Plant:
*Growth habit.*—Spreading.
*Plant height.*—15–25 cm.
*Plant extension.*—50–70 cm.
*Growth.*—Very vigorous with abundant branching and great profusion of blooms; the entire plant remaining in bloom for an extended period of time.

Stem:
*Diameter.*—2.0–3.0 mm.
*Anthocyanin pigmentation.*—Present.
*Branching.*—Abundant.
*Pubescence.*—Medium.
*Length of internode.*—4.0–5.0 cm.

Leaf:
*Phyllotaxis.*—Opposite.
*Shape of blade.*—Hastate.
*Length.*—4.0–5.0 cm.
*Width.*—2.0–2.5 cm.
*Depth of incision.*—Shallow.
*Color.*—Grayish olive green (R.H.S. 137A–137B, J.H.S. 3716).
*Pubescence.*—Slight.

Flower:
*Facing direction.*—Upward.
*Ourward curvature of petal.*—Curved.
*Diameter.*—1.5–2.0 cm.
*Height.*—20 mm.
*Color.*—Deep purplish pink (R.H.S. 70C, J.H.S. 9213).
*Color presentation.*—Uneven.
*Overlapping of petals.*—Separate.
*Spike.*—30–35 mm in length; and 50–55 mm in diameter.
*Calyx.*—1.0 cm in length.
*Anthocyanin pigmentation of calyx limb.*—Present.
*Peduncle.*—2–3 mm in thickness; and 5.0–6.0 cm in length.
*Number of flowers.*—Plentiful (approximately 13–15)
*Reproductive organs.*—1 pistil and 5 stamens.
*Flower fragrance.*—Absent.
*Flowering duration.*—Long.

Physiological and ecological characteristics: High resistance to diseases and pests, particularly powdery mildew. High tolerance to heat and moderate tolerance to cold.

'Derby Salmon Rose' (non-patent in the United States) was used as a comparison for this new variety 'Sunmarisa'. The main botanical characteristics of 'Derby Salmon Rose' are as follows when grown at the Hakushu Nursery Center of SUNTORY Ltd., 2913-1 Torihara, Hakushu-cho, Kitakoma-gun, Yamanashi-ken, Japan.

Plant:
*Growth habit.*—Semi-erect.
*Plant extension.*—Medium.

Stem:
*Anthocyanin pigmentation.*—Absent.
*Branching.*—Medium.
*Pubescence.*—Medium.
*Length of internode.*—Medium.

Leaf:
*Phyllotaxis.*—Opposite.
*Length.*—Medium.
*Width.*—Medium.
*Blode incision.*—Absent.
*Color.*—Dark green.
*Pubescence.*—Medium.

Flower:
*Facing direction.*—Upward.
*Outward curvature of petal.*—None.
*Diameter.*—Large.
*Height.*—Medium.
*Color.*—Vivid red (R.H.S. 52A, J.H.S. 0106).
*Color presentaion.*—Substantially even.
*Overlapping of petals.*—Closed.
*Cluster.*—Medium in length; and medium in diameter.
*Anthocyanin pigmentation of calyx limb.*—Present.
*Peduncle.*—Medium in thickness; and medium in length.
*Number of flowers.*—Medium.
*Reproductive organs.*—1 pistil and 5 stamens.
*Flower fragrance.*—Absent.
*Flowering duration.*—Medium.

Physiological and ecological charactgeristics: Weak resistance to diseases, heat and cold. Moderate resistance to pests.

This new variety of verbena plant 'Sunmarisa' was asexually reproduced by cuttings at the aforementioned Hakushu Nursery Center of SUNTORY Ltd., at 2913-1 Torihara, Hakushu-cho, Kitakoma-gun, Yamanashi-ken, Japan, and the homogeneity and stability thereof were confirmed. The characteristics of the new variety are fully stable following such asexual reproduction.

SUMMARY OF THE VARIETY

This new variety of verbena plant has a broad spreading growth habit and long stems. The plant is well branched and abundantly forms flowers in a cluster. The blooms are present in profusion. The blooming period is late April to November and flowering duration is long. The entire plant remains in bloom for an extended period of time. The flower size is large and the petal coloration of the flowers is light purplish pink. The plant is highly tolerant to heat, exhibits a high resistance to pests and diseases, particularly powdery mildew, and a high resistance to rain is exhibited.

DESCRIPTION OF THE VARIETY

Figure 1:
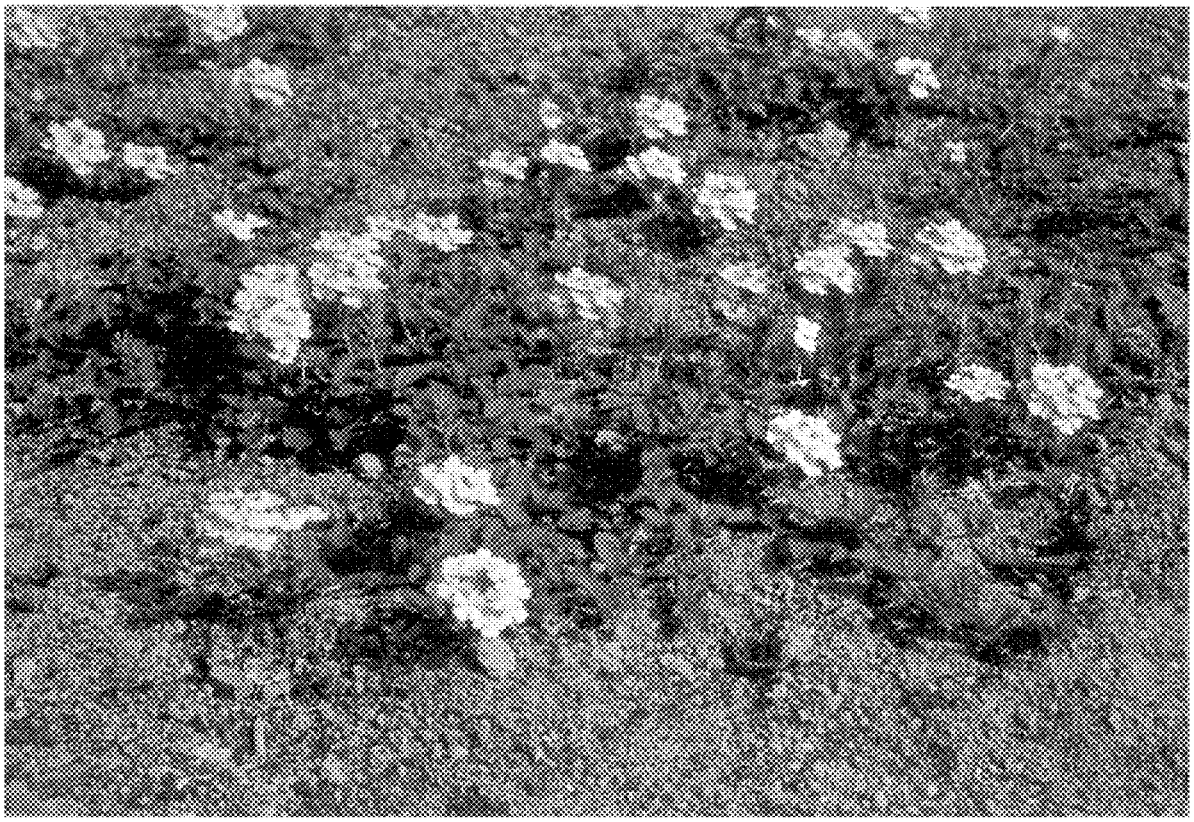
FIG. 1 depicts a side view of the 'Sunmarisa' plant of the present invention.
Figure 2:
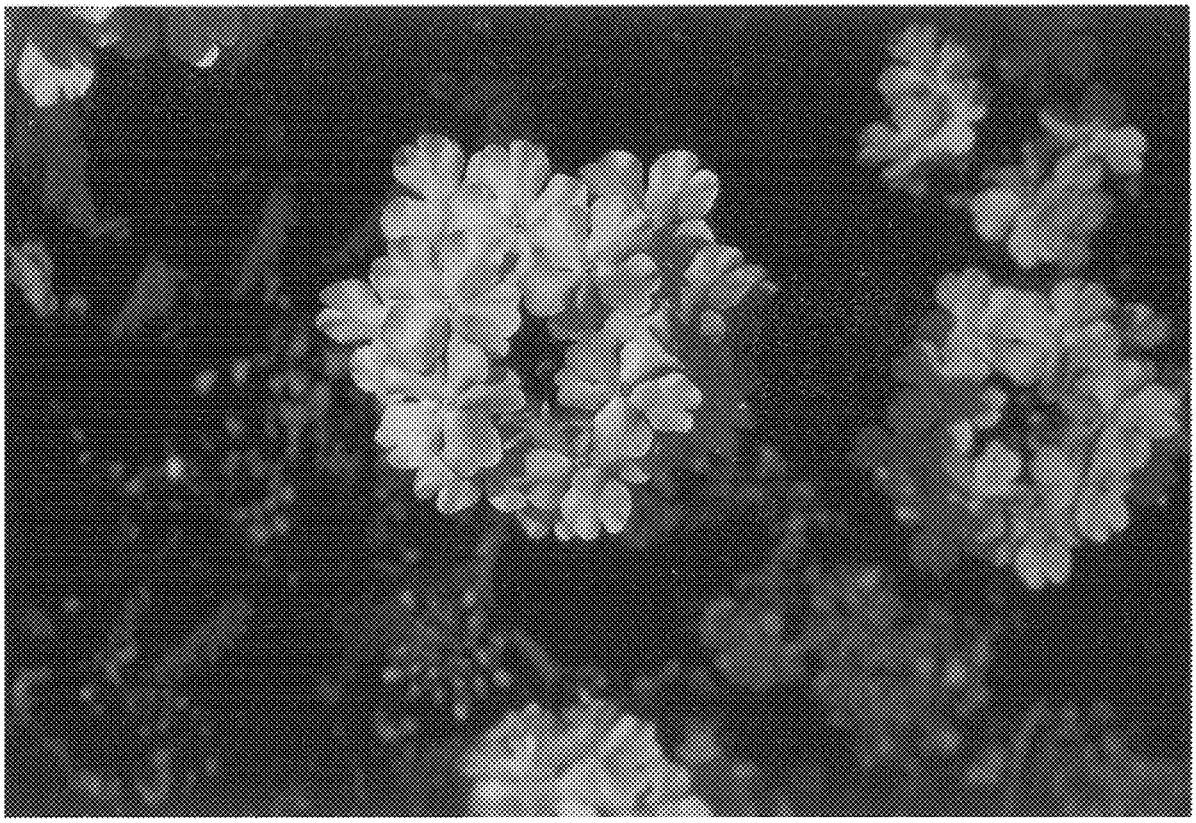
FIG. 2 depicts a close-up view of the flowers of the 'Sunmarisa' plant of the present invention.

The botanical characteristics of the new and distinct variety of verbena plant, 'Sunmarisa' are as follows when grown at the Hakushu Nursery Center of SUNTORY Ltd., 2913-1 Torihara, Hakushu-cho, Kitakoma-gun, Yamanashi-ken, Japan.

Plant:
- *Growth habit.*—Spreading.
- *Plant width.*—Broad; 65–71 cm.
- *Plant height.*—Very low to low; approximately 8–9 cm.

Stem:
- *Diameter.*—Medium; 1.7–2.2 mm.
- *Anthocyanin pigmentation.*—Absent.
- *Pubescence.*—Medium.
- *Branching.*—A moderate level of branching is present. Each single branch commonly produces two additional branches. More specifically, a single branch commonly becomes three branches and those three branches commonly produce nine branches, etc.
- *Color.*—R.H.S. 144A, J.H.S. 3507.
- *Subterranean stem.*—Absent. However, when the stems contact the surface of the soil, the nodes take root in the ground and the plant growth thereby spreads.
- *Length of internode.*—Medium; 1.7–2.7 cm.

Leaf:
- *Phyllotaxis.*—Opposite.
- *Shape of blade.*—Oblong-lanceolate.
- *Depth of blade incision.*—Shallow.
- *Blade margin.*—Doubly dentate.
- *Length.*—Medium; 2.9–3.6 cm.
- *Width.*—Medium; 1.6–2.4 cm.
- *Color.*—Dark olive green (R.H.S. 146A, J.H.S. 3707) on the upper surface and moderate yellow green (R.H.S. 144A and J.H.S. 3513 on the under surface).
- *Leaf apex.*—Mucronate.
- *Leaf base.*—Petiolate.
- *Pubescence.*—Slight.
- *Petiole.*—Present.
- *Petiole color.*—R.H.S. 144A, J.H.S. 3507.
- *Diameter of petiole.*—Medium; 1.0–1.2 mm.
- *Length of petiole.*—Short; 1.2–2.5 mm.

Flower:
- *Shape of cluster.*—Obovate.
- *Length of cluster.*—Medium; 23–44 mm.
- *Diameter of cluster.*—Medium; 40–58 mm.
- *Facing direction.*—Upward.
- *Outward curvature of petal.*—Slightly curved.
- *Diameter.*—Large; 1.8–1.9 cm.
- *Height.*—High; 2.1–2.2 cm.
- *Color.*—Light purplish pink (R.H.S. 62C, J.H.S. 9503) on the upper surface and light purplish pink (R.H.S. 65B, J.H.S. 9203) on the under surface. The petal coloration fades slightly with age.
- *Eye color.*—R.H.S. 11D, J.H.S. 2503.
- *Eye size.*—Small.
- *Color presentation.*—Substantially even.
- *Overlapping of petals.*—Separate.
- *Incision of petal.*—Present.
- *Number of petals.*—Medium; 5.
- *Sepals.*—Tubular in configuration.
- *Length of calyx.*—Long; 1.2–1.4 cm.
- *Anthocyanin pigmentation of calyx limb.*—Absent.
- *Color of anther.*—Yellow green.
- *Diameter of peduncle.*—Thin; 0.9–1.4 mm.
- *Length of peduncle.*—Medium; 19–45 mm.
- *Color of peduncle.*—Strong yellow green, R.H.S. 144A, J.H.S. 3507.
- *Number of flowers.*—Many; commonly 13±2.
- *Flower bearing.*—In a cluster (as illustrated).
- *Reproductive organs.*—1 pistil and 4 stamens.
- *Flower fragrance.*—Absent.
- *Flowering time.*—Early.
- *Flowering duration.*—Long.
- *Pollen.*—Brilliant greenish-yellow (R.H.S. 6C, J.H.S. 2704) in coloration. When planted during March, the plant commonly blossoms from April to November. A bloom cluster commonly is present for approximately 2 to 3 weeks, and an individual bloom wiithin the cluster commonly lasts for approximately 7 to 10 days on the plant.

Physiological and ecological characteristics: High resistance to diseases and pests, particularly powdery mildew. HIgh tolerance to heat and drought, high tolerance to rain, and medium tolerance to cold.

This new variety of Verbena plant is most suitable for flower bedding and potting, particularly in planters. It is further excellent for use as a ground cover.

We claim:

1. A new and distinct variety of Verbena plant having the FOLLOWING combination of characteristics:

(a) exhibits a broad spreading growth habit with long stems,
(b) forms in abundance clusters of attractive light purplish pink blossoms that remain on the plant for an extended period of time, and
(c) exhibits good tolerance to rain, heat, drought, and diseases;

substantially as shown and described.

* * * * *